US00PP27622P3

(12) United States Plant Patent
Caster et al.

(10) Patent No.: US PP27,622 P3
(45) Date of Patent: Jan. 31, 2017

(54) BLUEBERRY PLANT NAMED 'DRISBLUEFOURTEEN'

(50) Latin Name: ***Vaccinium corymbosum* L.**
Varietal Denomination: DrisBlueFourteen

(71) Applicant: DRISCOLL STRAWBERRY ASSOCIATES, INC., Watsonville, CA (US)

(72) Inventors: Brian K. Caster, Salinas, CA (US); Marta C. Baptista, Camarillo, CA (US); Bruce D. Mowrey, Watsonville, CA (US); Arlen Draper, Payson, AZ (US); Jennifer K. Izzo, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 103 days.

(21) Appl. No.: 14/544,671

(22) Filed: Feb. 2, 2015

(65) Prior Publication Data

US 2016/0227685 P1 Aug. 4, 2016

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Caster et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Caster et al. |
| PP26,537 | P3 | 3/2016 | Caster et al. |
| PP26,643 | P3 | 4/2016 | Caster et al. |
| PP26,748 | P3 | 5/2016 | Caster et al. |

OTHER PUBLICATIONS

Caster et al., U.S. Appl. No. 14/999,884, filed Jul. 13, 2016, titled "Blueberry plant variety named 'DrisBlueFifteen'".

*Primary Examiner* — Susan McCormick Ewoldt
(74) *Attorney, Agent, or Firm* — Morrison & Foerster LLP

(57) ABSTRACT

A new and distinct variety of blueberry plant named 'DrisBlueFourteen' particularly distinguished by having high productivity, strong cane renewal and large, firm berries with low acidity, is disclosed.

2 Drawing Sheets

Genus and species: *Vaccinium corymbosum* L.
Variety denomination: 'DrisBlueFourteen'.

BACKGROUND OF THE NEW PLANT

The invention relates to a new and distinct blueberry variety designated 'DrisBlueFourteen' and botanically known as *Vaccinium corymbosum* L. This new blueberry variety was discovered in Skagit County, Wash. in August 2004 and originated from a cross between the proprietary female parent blueberry plant 'G455' (unpatented) and the proprietary male parent blueberry plant 'MS122' (unpatented). The original seedling of the new variety was first asexually propagated at a nursery in Monterey County, Calif. in 2004. 'DrisBlueFourteen' was subsequently asexually propagated and underwent further testing at a nursery in Santa Cruz County, Calif. for five years. The present invention has been found to be stable and reproduce true to type through successive asexual propagations via softwood cuttings.

SUMMARY OF THE INVENTION

The following are the most outstanding and distinguishing characteristics of this new cultivar when grown under normal horticultural practices in Santa Cruz County, Calif.

1. High productivity;
2. Strong cane renewal; and
3. Large, firm berries with low acidity.

DESCRIPTION OF THE PHOTOGRAPHS

This new blueberry plant is illustrated by the accompanying photographs which show fruit of the plant as well as the flowers and leaves. The colors shown are as true as can be reasonably obtained by conventional photographic procedures. The photographs are of plants that are four years old.

DESCRIPTION OF THE NEW CULTIVAR

Figure 1:
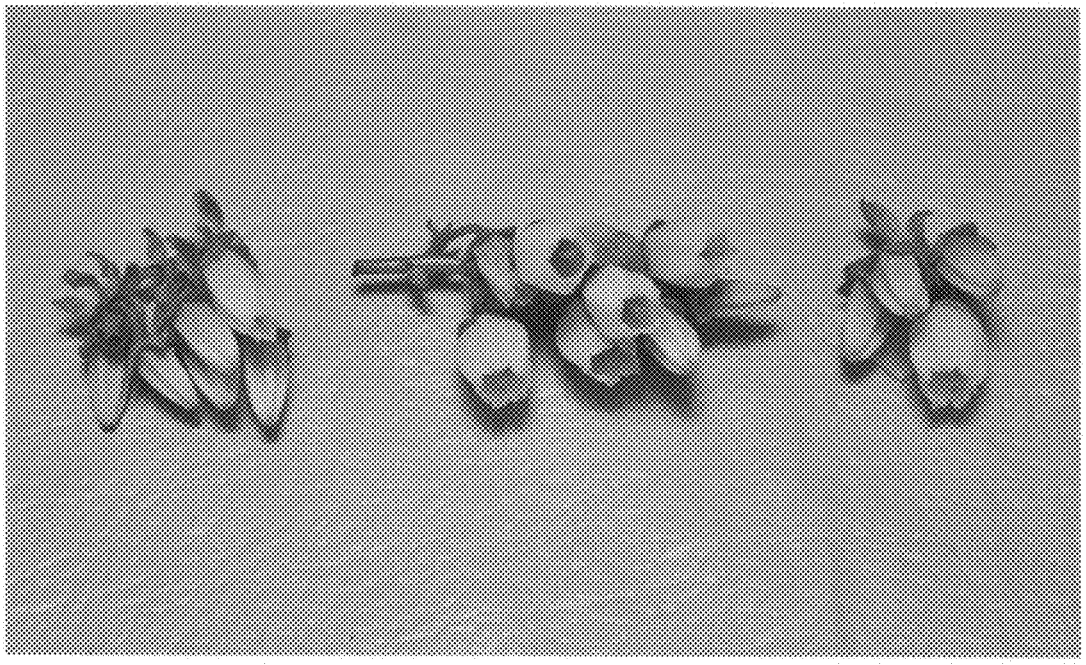
FIG. 1 shows a close-up of the mature flowers.
Figure 2:
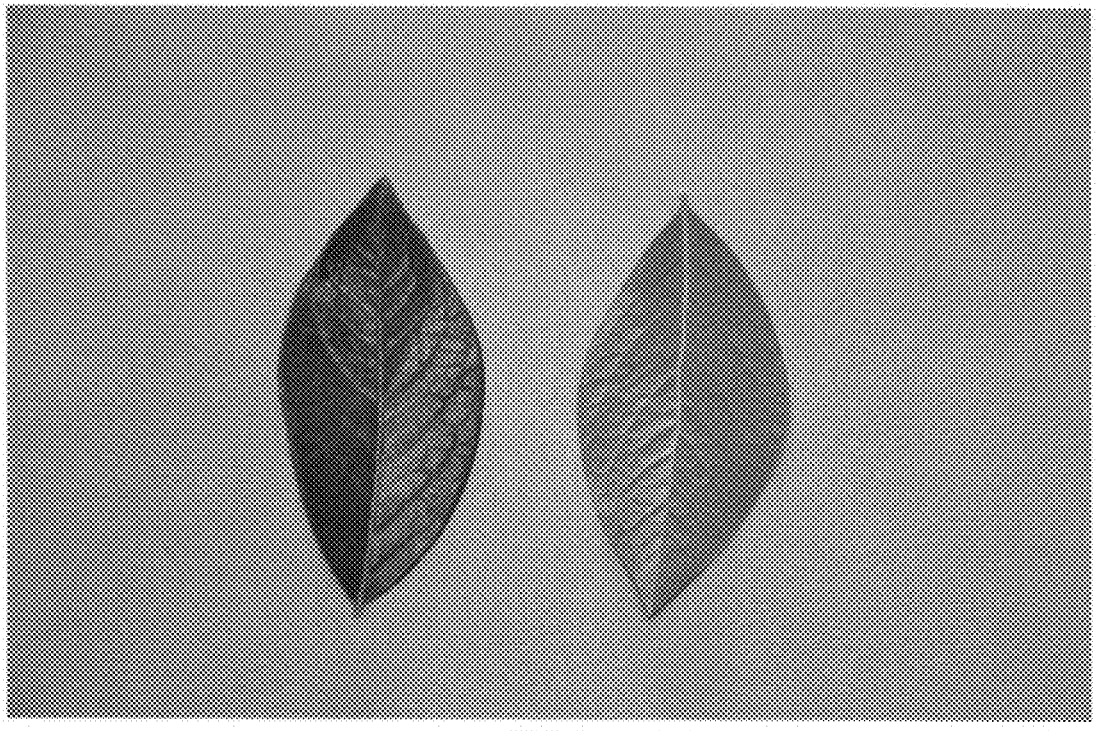
FIG. 2 shows a close-up of the upper and lower surfaces of the leaves.
Figure 3:
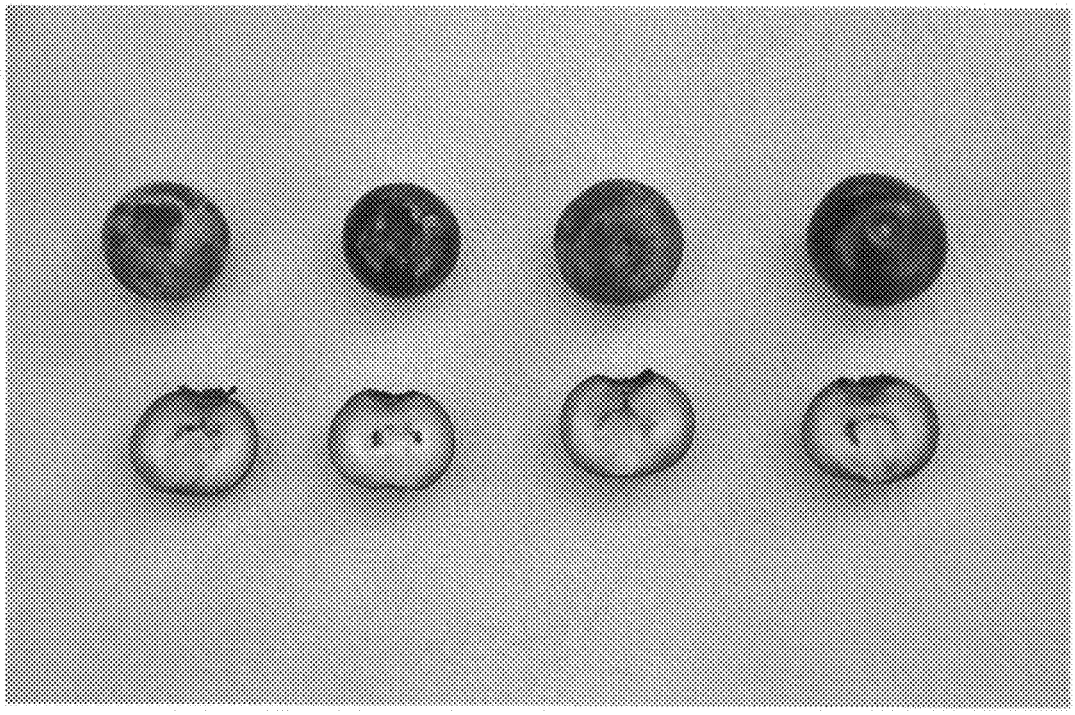
FIG. 3 shows a close-up of the whole fruit and a cross-section of the fruit.

The following detailed description sets forth the distinctive characteristics of 'DrisBlueFourteen'. The data which define these characteristics is based on observations taken in Santa Cruz County, Calif. from 2008-2012. This description is in accordance with UPOV terminology. Color designations, color descriptions, and other phenotypical descriptions may deviate from the stated values and descriptions depending upon variation in environmental, seasonal, climatic and cultural conditions. 'DrisBlueFourteen' has not been observed under all possible environmental conditions. The botanical description of 'DrisBlueFourteen' was taken from four year-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* 2$^{nd}$ edition by James G. Harris and Melinda Woolf Harris, unless where otherwise defined.

DETAILED BOTANICAL DESCRIPTION

Classification:
- *Family*.—Ericaceae.
- *Botanical*.—*Vaccinium corymbosum* L.
- *Common name*.—Blueberry.
- *Variety name*.—'DrisBlueFourteen'.

Parentage:
- *Female parent*.—The proprietary blueberry plant 'G455' (unpatented).
- *Male parent*.—The proprietary blueberry plant 'MS122' (unpatented).

Plant:
- *Size*.—Small.
- *Height*.—150.6 cm.
- *Width*.—167.9 cm.
- *Length/width ratio*.—0.9.
- *Plant vigor*.—Strong.
- *Growth habit*.—Semi-erect.
- *Productivity*.—3.85 kg of fruit per season from five-year old plants when grown in Albany, Oreg.
- *Cold hardiness*.—USDA Plant Hardiness Zones 8b to 7a.
- *Chilling requirement*.—850 to 1,000 hours below 45° F.
- *Propagation*.—Soft wood cuttings.
- *Time of vegetative bud burst*.—April.
- *Fruiting type*.—Only on one-year-old shoots.
- *Cane renewal*.—Strong.
- *Internode length* (*upper half on one-year old shoot*).—18.7 mm.
- *Young canes*.—Length: 100.0 cm. Diameter at the base: 10.4 mm. Diameter at the tip: 2.6 mm. Texture: Smooth. Color (One-year old shoot, branch and canes): RHS 144B (Medium yellow-green).
- *Mature canes*.—Length: 130.0 cm. Diameter at the base: 17.8 mm. Diameter at the tip: 4.1 mm. Texture: Rough. Color: RHS 197C (Light greyed-green).

Leaves:
- *Length*.—Medium; 8.34 cm.
- *Width*.—Medium; 4.04 cm.
- *Length/width ratio*.—2.1; Longer than broad.
- *Appearance of leaf bud*.—Medium.
- *Shape*.—Elliptic.
- *Apex*.—Acute.
- *Base*.—Cuneate.
- *Margin*.—Entire.
- *Glossiness*.—Medium.
- *Pubescence*.—Glabrous (Absent).
- *Sheath*.—Absent.
- *Arrangement*.—Alternate.
- *Venation*.—Reticulate.
- *Color*.—Upper surface: Dark; RHS 147A (Dark yellow-green). Lower surface: Medium; RHS 191B (Medium greyed-green).
- *Internode length* (*one-year old shoot, upper half*).—18.7 mm.

Petiole:
- *Length*.—5.1 mm.
- *Diameter*.—1.21 mm.
- *Color*.—RHS 145C (Light yellow-green).

Flowers:
- *Length* (*excluding peduncle*).—Medium; 10.53 mm.
- *Diameter*.—7.20 mm.
- *Length/width ratio*.—1.5.
- *Color*.—RHS 157B (Light green-white).
- *Flower bud*.—Length: 7.5 mm. Width: 5.1 mm. Number of flowers per bud or peduncle: 7. Color on mature buds: Light; RHS 155B (White) and 65C (Light red-purple).
- *Petal width*.—4.91 mm.
- *Fragrance*.—Very faint or absent.
- *Time of beginning flowering on one-year shoot*.—Late.
- *Time of flowering* (50% *antithesis or full bloom*).—Medium.
- *Flowering interval*.—Mid-April to early May.
- *Pedicel*.—Length: 8.45 mm. Diameter: 1.04 mm. Color: RHS 142B (Medium green).
- *Corolla*.—Aperture diameter: 3.88 mm. Shape: Urceolate (Urn-shaped). Anthocyanin coloration of corolla tube: Medium; RHS 63B (Medium red-purple). Ridges on tube: Present.
- *Peduncle length*.—4.44 mm.

Reproductive organs:
- *Style length* (*including stigma*).—Medium; 10.61 mm.
- *Style color*.—RHS 141D (Medium green).
- *Pollen amount*.—Low to medium.
- *Pollen color*.—RHS 4D (Light yellow).
- *Anther color*.—RHS 167B (Medium greyed-orange).
- *Ovary color*.—RHS 191A (Medium greyed-green).
- *Pollination requirement*.—Intermediate.

Fruit:
- *Size*.—Large.
- *Length*.—14.09 mm.
- *Width*.—17.15 mm.
- *Length/width ratio*.—0.8.
- *Fruit pedicel diameter*.—3.18 mm.
- *Fruit weight* (g).—2.2.
- *Cluster density*.—Medium.
- *Shape in longitudinal sections*.—Oblate.
- *Intensity of green color* (*immature fruit with bloom*).—Light or clear; RHS 149D (Light yellow-green).
- *Color of skin* (*immature fruit without bloom*).—RHS N92A (Dark violet-blue).
- *Color of skin* (*mature fruit without bloom*).—RHS 202A (Black).
- *Color of skin* (*mature fruit with bloom*).—RHS 102B (Medium blue).
- *Intensity of bloom* (*mature fruit*).—Strong.
- *Attitude of sepals*.—Prostrate (Reflexed).
- *Calyx*.—Diameter of basin: Medium; 5.41 mm. Depth of basin: Medium; 4.17 mm. Calyx basin diameter/depth ratio: 1.3.
- *Flesh color*.—RHS 145C (Light yellow-green).
- *Firmness*.—Firm.
- *Sweetness*.—Medium.

*Acidity*.—Low.

*Time of beginning of fruit ripening* (*one-year old shoots*).—June.

*Harvest season*.—Late.

*Harvest interval*.—Late June-late July.

*Shipping and storage characteristics*.—Fruit can be stored for 21 days at 0° C.

*Market use*.—Fresh market.

Seeds:

*Length*.—1.81 mm.

*Width*.—0.93 mm.

*Length/width ratio*.—1.9.

*Abundance*.—Low.

*Color*.—RHS 166B (Medium greyed-orange).

COMPARISON WITH PARENTAL AND COMMERCIAL VARIETIES

When 'DrisBlueFourteen' is compared to male parent 'MS122' (unpatented), 'MS122' is a more bushy and vigorous plant than 'DrisBlueFourteen'. In addition, 'DrisBlueFourteen' is a Northern Highbush, whereas 'MS122' is a Southern Highbush.

When 'DrisBlueFourteen' is compared to female parent 'G455' (unpatented), 'G455' produces more spherical-shaped fruit than 'DrisBlueFourteen'. In addition, fruit of 'DrisBlueFourteen' has a higher sweetness than fruit of 'G455'.

'DrisBlueFourteen' is similar to commercial variety 'Elliott' (unpatented). 'DrisBlueFourteen' differs from 'Elliott' in that 'DrisBlueFourteen' has a semi-erect growth habit, whereas 'Elliott' has an upright growth habit. Additionally, 'DrisBlueFourteen' has large-sized, medium blue berries, whereas 'Elliott' has medium-sized, light blue berries.

'DrisBlueFourteen' is similar to commercial variety 'Bluecrop' (unpatented). 'DrisBlueFourteen' differs from 'Bluecrop' in that 'DrisBlueFourteen' has a semi-erect growth habit, whereas 'Bluecrop' has an upright growth habit. Additionally, 'DrisBlueFourteen' has medium blue berries with medium sweetness, whereas 'Bluecrop' has light blue berries that are slightly tart.

'DrisBlueFourteen' differs from commercial blueberry plant variety 'DrisBlueEleven' (U.S. Plant Pat. No. 26,537) in that plants of 'DrisBlueFourteen' are smaller and have higher vigor than plants of 'DrisBlueEleven'. 'DrisBlueFourteen' also has greater cold hardiness than 'DrisBlueEleven'. The productivity of 'DrisBlueFourteen' is higher than that of 'DrisBlueEleven'. 'DrisBlueFourteen' also produces more flowers per bud or peduncle than does 'DrisBlueEleven'. Further, the fruit of 'DrisBlueFourteen' are larger with higher clustering density than fruit of 'DrisBlueEleven'. Additionally, fruit of 'DrisBlueFifteen' has a higher sweetness than fruit of 'DrisBlueEleven'.

We claim:

1. A new and distinct variety of blueberry plant named 'DrisBlueFourteen', substantially as illustrated and described herein.

* * * * *